[12] United States Patent
Hartman et al.

(10) Patent No.: US 9,114,255 B1
(45) Date of Patent: Aug. 25, 2015

(54) EXERCISE DEVICE FOR USE WITH ELECTRICAL STIMULATION AND RELATED METHODS

(75) Inventors: Eric C. Hartman, Lexington, KY (US); L. Gentry Barnett, Lexington, KY (US); Tarik S. Aweimrin, Lexington, KY (US); John D. Alton, Versailles, OH (US)

(73) Assignee: CUSTOMKYNETICS, INC., Versailles, KY (US)

( * ) Notice: Subject to any disclaimer, the term of this patent is extended or adjusted under 35 U.S.C. 154(b) by 470 days.

(21) Appl. No.: 13/525,699

(22) Filed: Jun. 18, 2012

Related U.S. Application Data

(60) Provisional application No. 61/498,303, filed on Jun. 17, 2011.

(51) Int. Cl.
  *A61N 1/36* (2006.01)
  *A63B 21/002* (2006.01)
  *A63B 21/00* (2006.01)
  *A61B 5/11* (2006.01)
  *A61B 5/00* (2006.01)

(52) U.S. Cl.
  CPC .......... *A61N 1/36003* (2013.01); *A61B 5/1107* (2013.01); *A61N 1/3615* (2013.01); *A61N 1/36139* (2013.01); *A63B 21/0023* (2013.01); *A63B 21/00156* (2013.04); *A61B 5/6828* (2013.01)

(58) Field of Classification Search
  None
  See application file for complete search history.

(56) References Cited

U.S. PATENT DOCUMENTS

| | | | |
|---|---|---|---|
| 3,188,139 A * | 6/1965 | Boyce | 297/466 |
| 4,165,750 A | 8/1979 | Aleev et al. | |
| 4,421,336 A * | 12/1983 | Petrofsky et al. | 280/252 |
| 4,480,830 A | 11/1984 | Petrofsky et al. | |
| 4,492,233 A | 1/1985 | Petrofsky et al. | |
| 4,586,495 A * | 5/1986 | Petrofsky | 602/2 |
| 4,838,272 A | 6/1989 | Lieber | |
| 5,070,873 A | 12/1991 | Graupe et al. | |
| 5,507,788 A | 4/1996 | Lieber | |
| 5,540,735 A | 7/1996 | Wingrove | |
| 5,628,722 A | 5/1997 | Solomonow et al. | |
| 5,643,332 A | 7/1997 | Stein | |
| 6,056,675 A * | 5/2000 | Aruin et al. | 482/91 |
| 6,324,432 B1 | 11/2001 | Rigaux et al. | |
| 6,456,884 B1 | 9/2002 | Kenney | |
| 6,456,885 B1 | 9/2002 | Shiba et al. | |
| 6,517,503 B1 | 2/2003 | Naft et al. | |
| 6,725,094 B2 | 4/2004 | Saberski | |
| 6,770,045 B2 | 8/2004 | Naft et al. | |
| 6,872,187 B1 | 3/2005 | Stark et al. | |

(Continued)

FOREIGN PATENT DOCUMENTS

JP 2006325755 A * 12/2006

*Primary Examiner* — Kennedy Schaetzle
(74) *Attorney, Agent, or Firm* — King & Schickli, PLLC

(57) ABSTRACT

A device includes a brace that may be used in conjunction with neuromuscular electrical stimulation to induce isometric contractions in one or more muscles of a subject's limb muscles by way of a series of stimulation cycles. The device may include a controller for stimulating the leg muscles, and for autonomously adjusting the stimulation based on a measured force exerted by the leg on the brace. The controller may adjust the stimulation based on the measured force from a previous cycle as compared with a goal force. Additionally, the adjustment may be based on the comparison of the measured force within that cycle to the goal force, analyzed on a continuous basis within that cycle.

22 Claims, 10 Drawing Sheets

(56) References Cited

U.S. PATENT DOCUMENTS

| | | |
|---|---|---|
| 7,204,814 B2 | 4/2007 | Peles |
| 7,257,448 B2 | 8/2007 | Crowe et al. |
| 7,337,007 B2 | 2/2008 | Nathan et al. |
| 7,367,958 B2 | 5/2008 | McBean et al. |
| 7,410,471 B1 | 8/2008 | Campbell et al. |
| 7,416,537 B1 | 8/2008 | Stark et al. |
| 7,499,746 B2 | 3/2009 | Buhlmann et al. |
| 7,899,556 B2 | 3/2011 | Nathan et al. |
| 2004/0039426 A1* | 2/2004 | Hurtado .......................... 607/48 |
| 2005/0283205 A1 | 12/2005 | Lee et al. |
| 2008/0216570 A1* | 9/2008 | Andres et al. .............. 73/379.01 |
| 2009/0105795 A1 | 4/2009 | Minogue et al. |
| 2009/0171417 A1 | 7/2009 | Philipson |
| 2009/0287126 A1 | 11/2009 | Skahan et al. |
| 2010/0137108 A1* | 6/2010 | Jaquish et al. .................... 482/9 |
| 2010/0280500 A1 | 11/2010 | Skelton et al. |

* cited by examiner

FIG. 6a
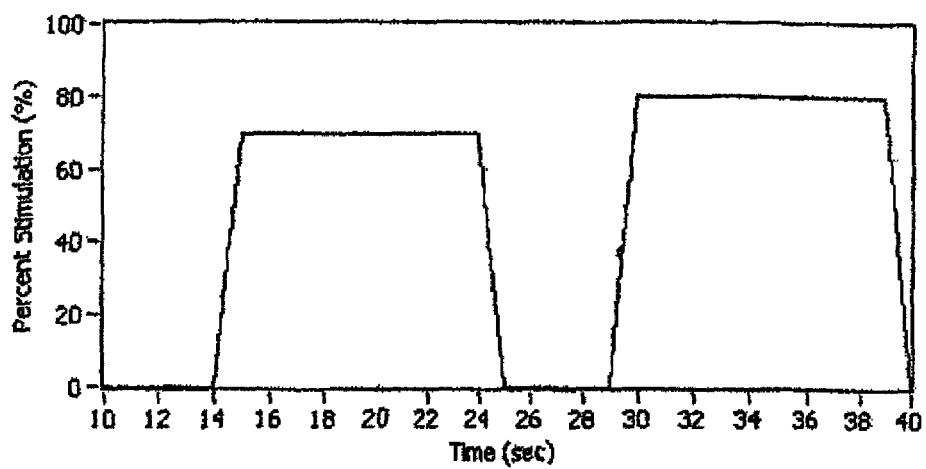
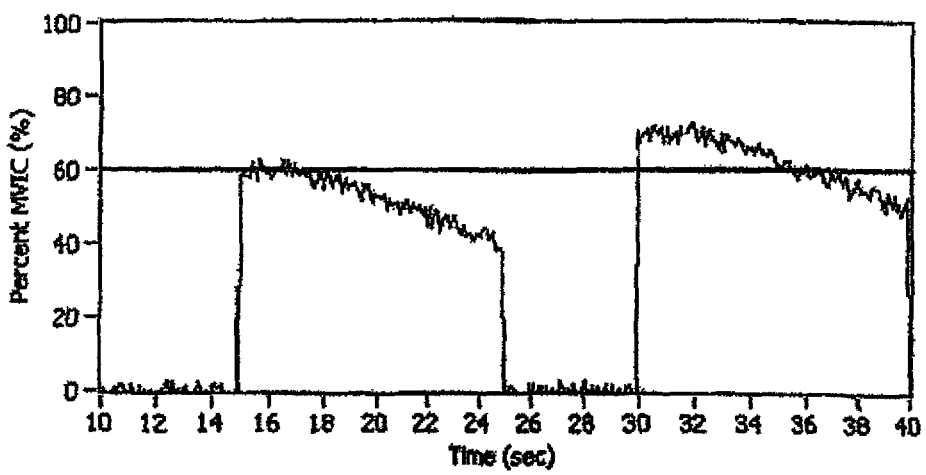
FIG. 6b

FIG. 7a
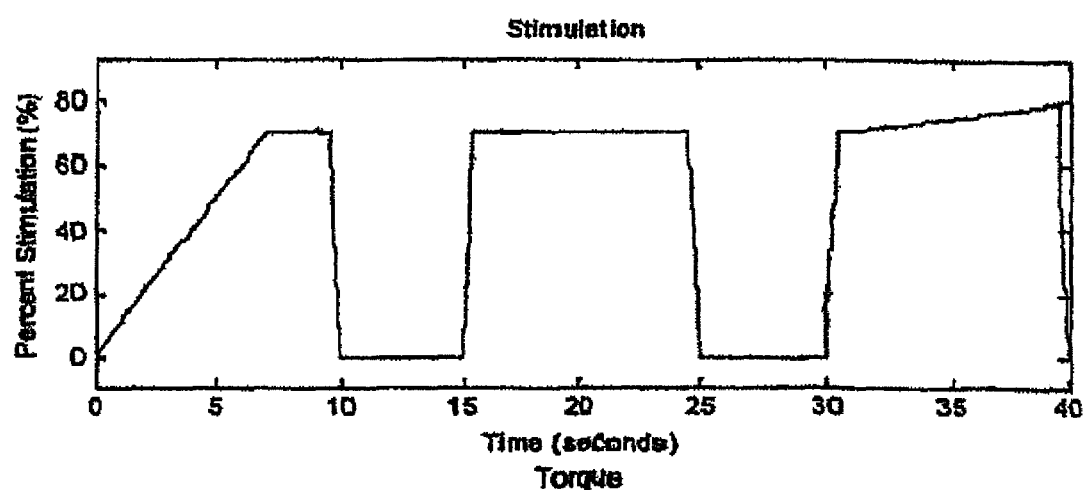
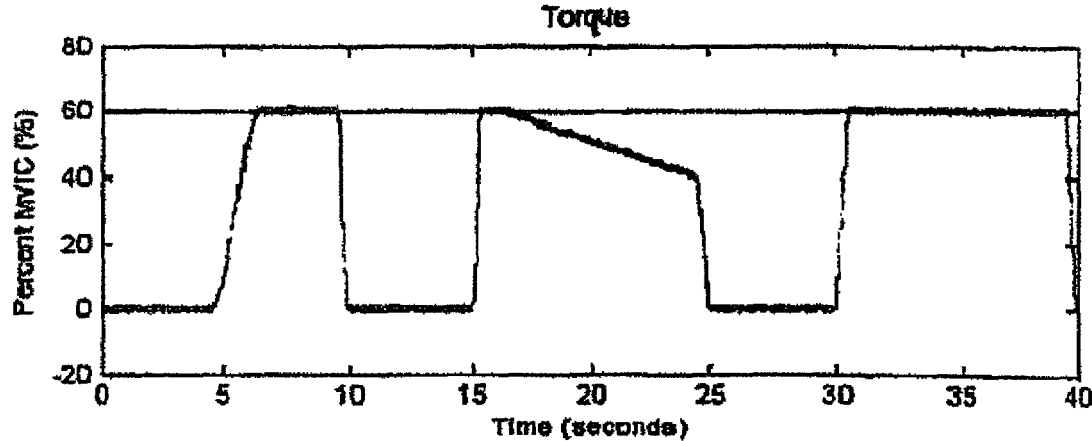
FIG. 7b

EXERCISE DEVICE FOR USE WITH ELECTRICAL STIMULATION AND RELATED METHODS

This application claims the benefit of U.S. Provisional Patent Application Ser. No. 61/498,303, filed Jun. 17, 2011, the disclosure of which is incorporated herein by reference.

STATEMENT OF GOVERNMENT SUPPORT

This invention was supported by a grant from the National Institute of Health under contract number 4R44HD055019-02. The government may have certain rights in this invention.

This invention was made with an award from the Kentucky Cabinet for Economic Development, Department of Commercialization and Innovation, under Grant Agreement KSTC-184-512-08-050 with the Kentucky Science and Technology Corporation.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present disclosure relates to the human exercise and rehabilitation arts, and, more particularly, to a brace for use in conjunction with electrical stimulation.

BACKGROUND

Electrical stimulation is a fundamental therapeutic modality that is indicated for pain management (TENS), drug delivery (Ionophoresis), and for treatment of a variety of neuromuscular conditions. Various terms are used to refer to electrical stimulation depending on the application and stimulus waveform used. Electrical stimulation with intensities sufficient to cause tetaneous contractions of skeletal muscle may result in muscle strengthening and/or joint/limb movement, and is termed Neuromuscular Electrical Stimulation (NMES) or Functional Electrical Stimulation (FES).

Electrical stimulation systems generate sequences of current pulses which excite motor neurons and in turn activate muscles. By changing the width, amplitude, or the frequency of the pulse train, the level of contraction can be altered to perform a specific task. In fitting an NMES system to an individual, a large set of parameters must be modified to account for each person's specific injury, anatomy, and muscle condition. The procedure for specifying these parameters requires a time-consuming trial-and-error process to find an appropriate set of parameters for each muscle. Since the same pulse train will be delivered for each contraction, the set of parameters that is suitable at the beginning of a session may not be appropriate after muscles fatigue. Similarly, day-to-day variability, nonlinearities of the musculoskeletal system, muscle response time, muscle conditioning, and joint constraints may hinder the effectiveness of even the best stimulation patterns.

Recovery of quadriceps muscle force following post-surgical knee immobilization is a significant therapeutic aim which is associated with quality of gait and the ability to perform activities of daily living. Several studies from various research groups have shown that neuromuscular electrical stimulation (NMES), used in conjunction with a comprehensive post-surgical rehabilitation program, is a safe and highly effective method for achieving quadriceps strengthening. Electrical stimulation has been widely studied as a technique indicated for quadriceps muscle strengthening for anterior cruciate ligament reconstruction (ACLR), total knee arthroplasty (TKA), and osteoarthritis. Efficacy of NMES for this application has been somewhat controversial, particularly in relation to the exercise protocol. Muscle strengthening outcomes of electrically stimulated exercise result not from the electrical stimulation itself but from the resulting muscle contraction; thus, stimulation protocols that do not elicit strong muscle contractions will have limited ability to build muscle.

Accordingly, it is desirable to develop a low cost, practical, cohesive system for quadriceps strengthening involving an NMES unit with autonomous, adaptive stimulation control capabilities in an outcome-based paradigm that does not require continuous involvement of the therapist. Another objective is to develop such a system that autonomously accounts for muscle fatigue during the exercise. A further goal is to develop an instrumented knee brace for use in such a system, capable of stabilizing the knee during near maximal isometric contractions and obtaining measurements of the resulting torque.

SUMMARY

In one embodiment, the disclosure relates to a device for use by a human subject in a seated, upright condition in conjunction with one or more electrodes for transmitting electrical stimulation from a stimulator to at least one muscle of a leg to perform an isometric contraction of the muscle. The device may comprise a brace including a seat adapted for receiving and supporting an upper portion of the leg of the subject in the seated, upright condition, said brace also including a lower extension depending from the seat and configured to constrain a lower portion of the leg. A stimulator is provided for transmitting electrical stimulation to at least one muscle to cause the isometric contraction of the muscle.

In one aspect, a hinge may be provided for fixing the lower extension relative to the seat and determining an amount of knee flexion during the isometric contraction. The lower extension may include at least one arm supporting a transverse member for engaging a front side of the lower leg, the position of the transverse member being adjustable along the lower extension. The seat may further comprise a first end portion adapted for positioning adjacent a rear surface of the subject's knee joint while the transverse member engages the front side of the lower leg. The device may further include at least one strap for securing the upper portion of the leg to the seat.

In another aspect, the device may include an instrumented brace, which may comprise a sensor for sensing a force exerted against the brace during or resulting from the isometric contraction. The device may further include a controller for controlling the stimulation through the electrodes based at least partially on the sensed force. This controller may be adapted to compare a sensed force during a first contraction cycle to a predetermined force goal and to adjust the stimulation during a subsequent contraction cycle based on said sensed force. The controller may be further adapted to compare the sensed force within the contraction cycle to a predetermined force goal, and if the sensed force is below the predetermined force goal, increase the stimulation within that contraction cycle based on the sensed force.

In another embodiment, a method is disclosed for stimulating a leg of a human subject to cause an isometric contraction in at least one leg muscle. The method may include the step of constraining the movement of the subject's leg using a brace, the subject being seated at least partially along an upper portion of the brace connected to a lower portion of the brace for receiving the subject's lower leg. The method may further include the step of electrically stimulating the subject's leg in order to cause the isometric contraction and urge the lower leg against the lower portion of the brace.

In one aspect, the stimulation step comprises stimulating the leg muscle with a first pulse train during a first cycle. The method may further include measuring a torque exerted by the leg during the first cycle, and adjusting a second pulse train during a second cycle to stimulate the subject's leg at a stimulation level based at least partially on the measured torque during the first cycle. In one aspect, the adjusting step comprises comparing an average measured torque during the first cycle to a goal torque. The method may further include measuring a torque during the second cycle, and wherein the adjusting step further includes adjusting the second pulse train based at least partially on the measured torque during the second cycle. The adjusting step may comprise comparing the measured torque during the second cycle to a goal torque and increasing or decreasing the stimulation level of the second pulse train to cause the measured torque to approximate the goal torque. The comparing step may comprise comparing the measured torque to the goal torque at a series of time intervals within the second cycle.

In another aspect, the method may further include the step of providing at least one initial warm-up cycle that gradually increases the stimulation until a value of the measured torque equals a goal torque. In another aspect, the method may include the step of increasing the stimulation during the second cycle to compensate for fatigue. In a further aspect, the method may further include the step of fixing the leg at between about 60 degrees to about 65 degrees of knee flexion.

In another embodiment according to the disclosure, a method is disclosed for adaptively stimulating a limb of a human subject during a series of neuromuscular electrical stimulation cycles, wherein each cycle comprises a plurality of stimulation pulses. The method includes providing a brace adapted for electrically stimulating the limb in a first cycle using a first pulse train to elicit a muscular contraction, determining an actual force applied by the muscular contraction during the first cycle, and electrically stimulating the limb at a first time interval in a second cycle using a second pulse train different from the first pulse train to stimulate the limb based at least partially on the actual force determined during the first cycle.

The method may further include the step of increasing the stimulation at a second time interval in the second cycle in response to the measured force at the first time interval being lower than a goal force, and decreasing the stimulation at the second time interval in response to measured force at the first time interval being greater than the goal force. In another aspect, the step of determining an actual force includes the step of calculating an average measured force in the first cycle, and the second stimulation step comprises comparing that average measured force to the goal force.

A further embodiment of the present invention includes an instrumented brace for adaptively stimulating a limb of a human subject during a series of neuromuscular electrical stimulation cycles, each cycle comprising a plurality of stimulation pulses. The brace may comprise a sensor for measuring a force exerted by the subject on the brace and a controller adapted for electrically stimulating the limb in a first cycle using a first pulse train to elicit a muscular contraction, and for electrically stimulating the limb at a first time interval in a second cycle using a second pulse train different from the first pulse train to stimulate the limb based at least partially on a measured force during the first cycle.

In one aspect, the controller is further adapted to increase the stimulation at a second time interval in the second cycle in response to the measured force at the first time interval being lower than a goal force, and decreasing the stimulation at the second time interval in response to measured force at the first time interval being greater than the goal force.

In another aspect, the controller is further adapted to calculate an average measured force in the first cycle, and to provide the stimulation at the first time interval in the second cycle based on a comparison of the average measured force during the first cycle to the goal force.

BRIEF DESCRIPTION OF THE DRAWINGS

FIGS. 6a and 6b are graphs of stimulation and measured force;

FIGS. 7a and 7b are graphs of stimulation and measured force; and

DETAILED DESCRIPTION

Figure 1:
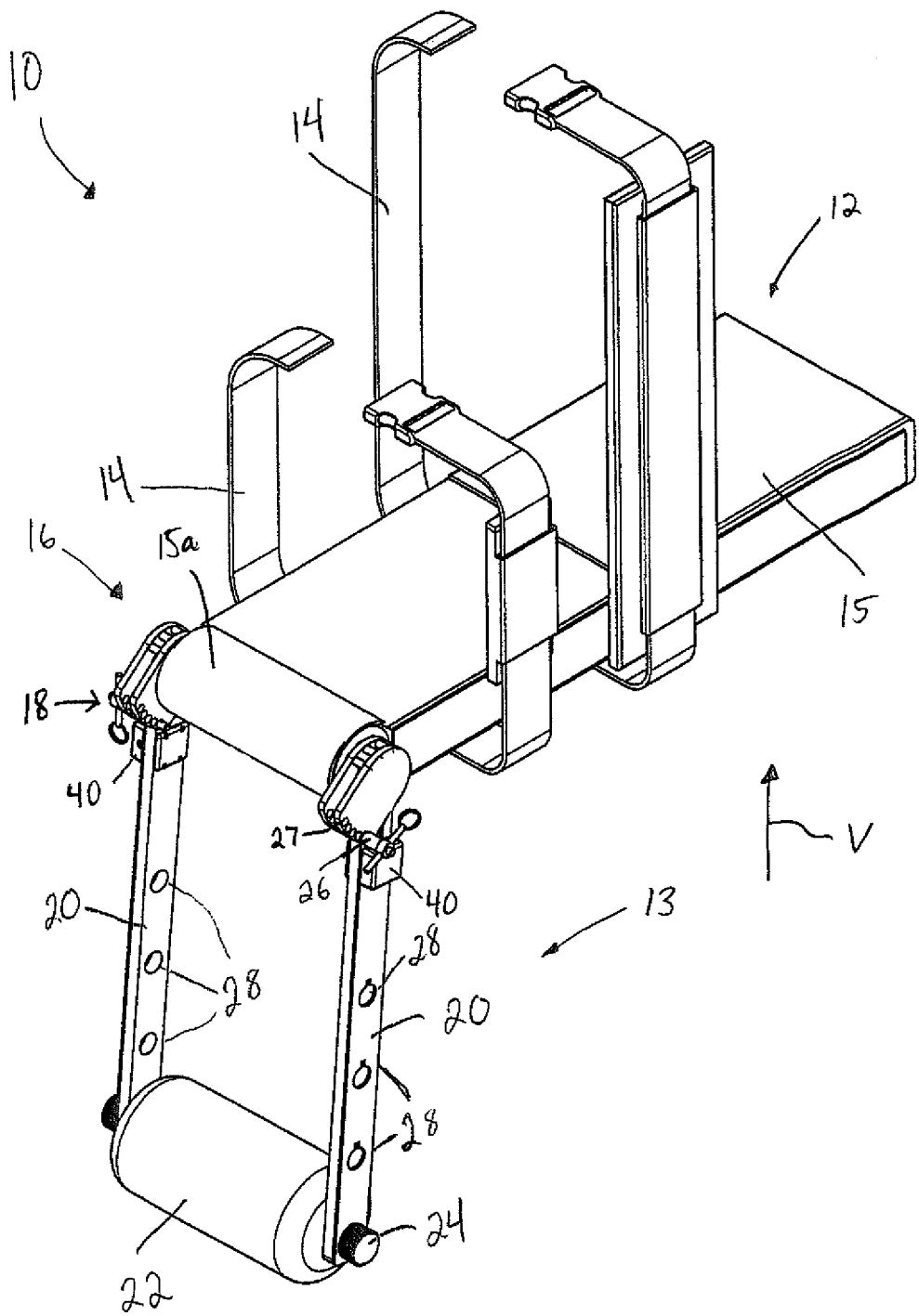
FIG. 1 is a perspective view of one embodiment of a device forming one aspect of the disclosure.
Figure 1A:
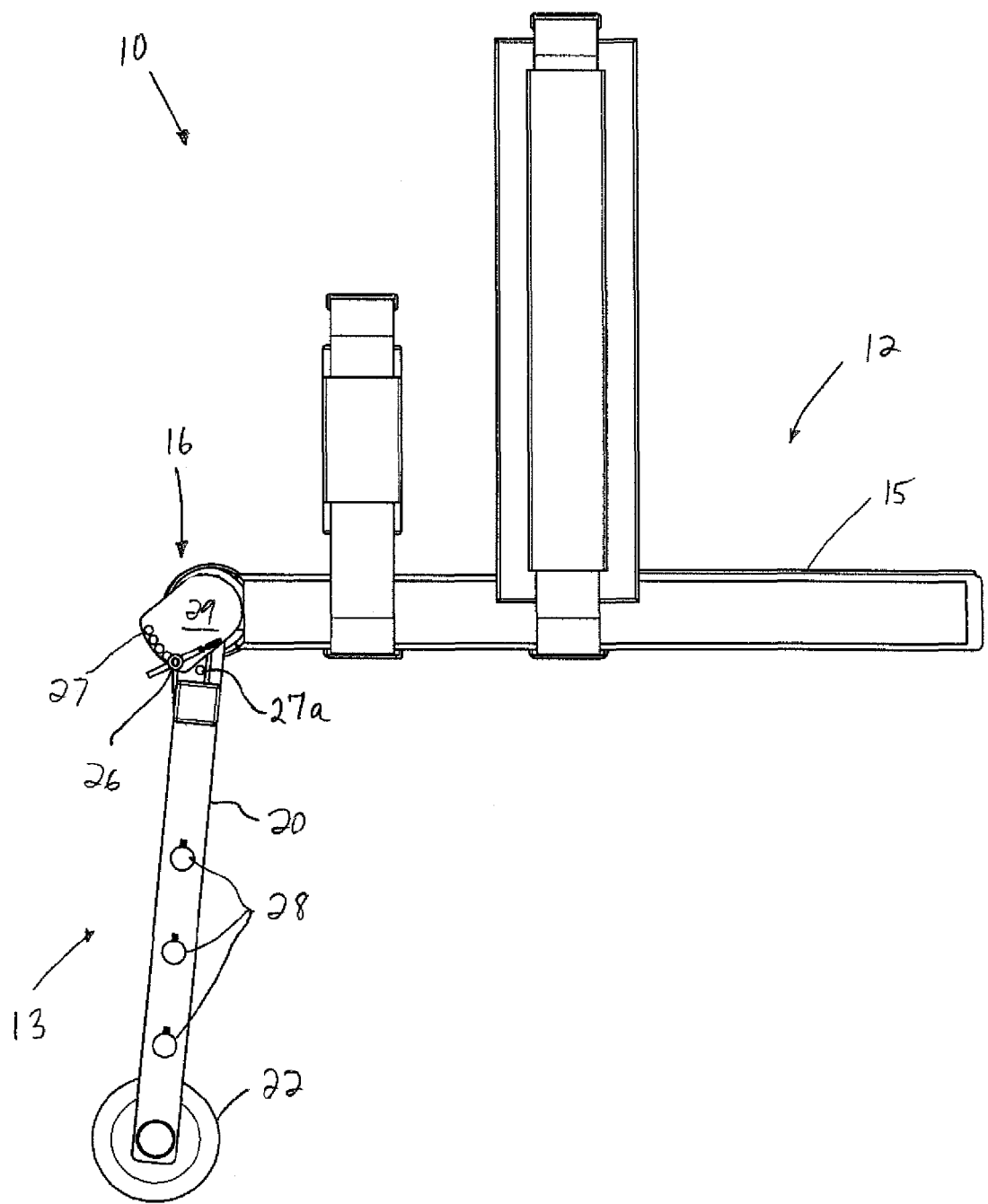
FIG. 1a is a side view of the device of FIG. 1.
Figure 1B:
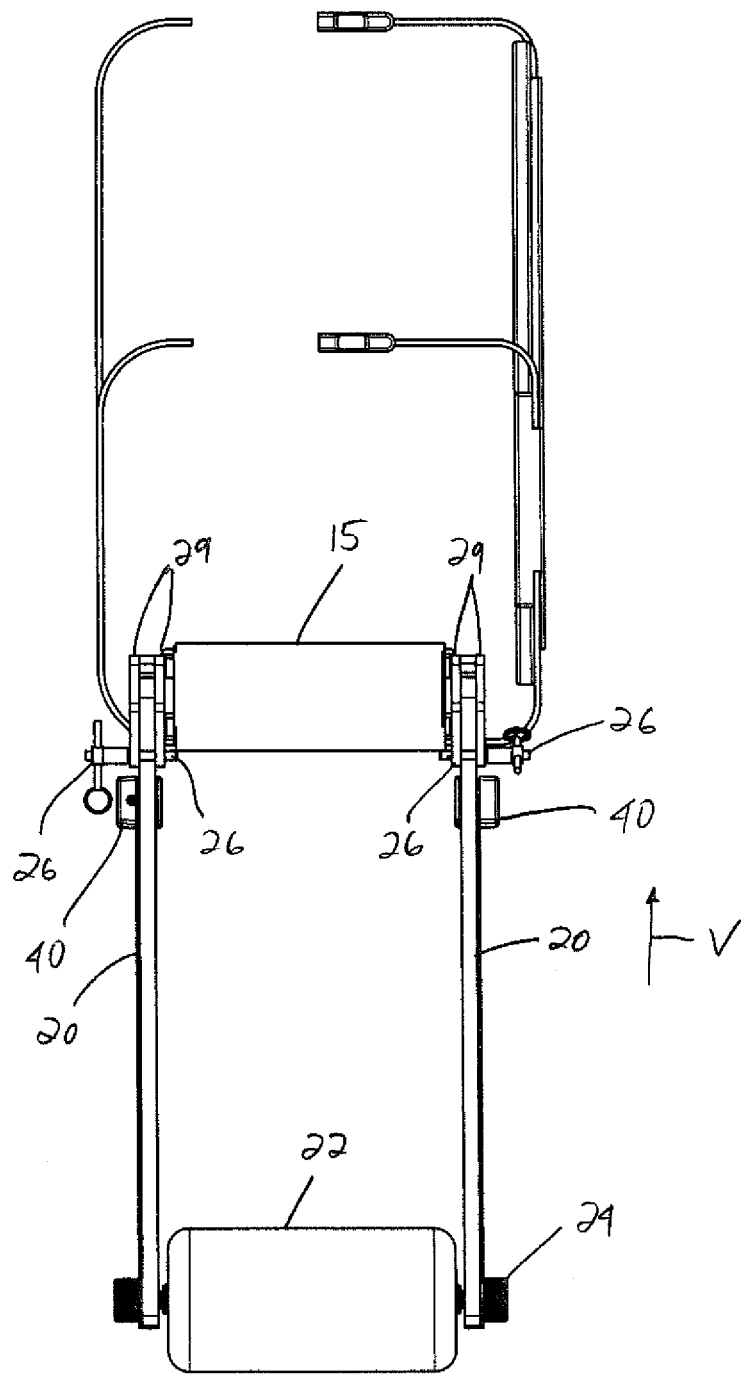
FIG. 1b is front view of the device of FIG. 1.

Reference is now made to FIGS. 1, 1a, 1b and 2, which together illustrate one embodiment of an exercise device in the form of a brace 10 for use in conjunction with applied stimulation, such as neuromuscular electrical stimulation (NMES). The brace 10 may be used by a subject with a joint in need of exercise or rehabilitation, such as for example the knee joint. Generally, the subject's joint is stabilized using the brace 10 to obtain an isometric exercise environment (that is, one that results in a muscular contraction against resistance without change in the joint angle, in this case afforded by the brace), which may be repeated periodically.

The brace 10 may be specially adapted for use in connection with the subject's leg, and may be configured for use alternately on either the right leg or left leg. In a particular embodiment adapted for leg use, the brace 10 comprises an upper portion or base in the form of a seat 12 on which the subject may be seated during the use of the device. In the illustrated embodiment, it can be understood that the seat 12 comprises a relatively narrow, elongated support platform 15 for receiving and supporting the upper leg while the subject is in a seated, upright position.

Optionally, the platform 15 includes a first end portion having a rounded front face 15a for comfortably engaging the back of the leg adjacent to the knee joint when the lower leg depends therefrom. The seat 12 may further include a retainer, such as one or more straps 14, for securing the subject's upper leg to the platform 15. This retention helps to facilitate the isometric contraction and reduce the influence of externally applied forces, such as from uninvolved muscles.

A lower extension 13 depends from the seat 12 for receiving the lower portion of the leg (which as should be appreciated will be generally lower in vertical position (note arrow V) than the subject's upper leg when positioned on the platform 15). The seat 12 and extension 13 may be connected by a connector permitting a limited degree of relative movement, such as a hinge 16 having a plurality of pre-determined fixed positions for purposes of adjustment, as outlined further in the following description. The extension 13 may also be adapted for engaging and holding the subject's lower leg in a fixed position relative to the brace 10. For instance, a cross member 22 may be provided for positioning in front of the shin or otherwise along the front portion of the lower leg during use of the brace 10. In one aspect, the cross member 22 may be supported on either side by elongated arms 20 extending from the base of the brace 10.

Figure 2:
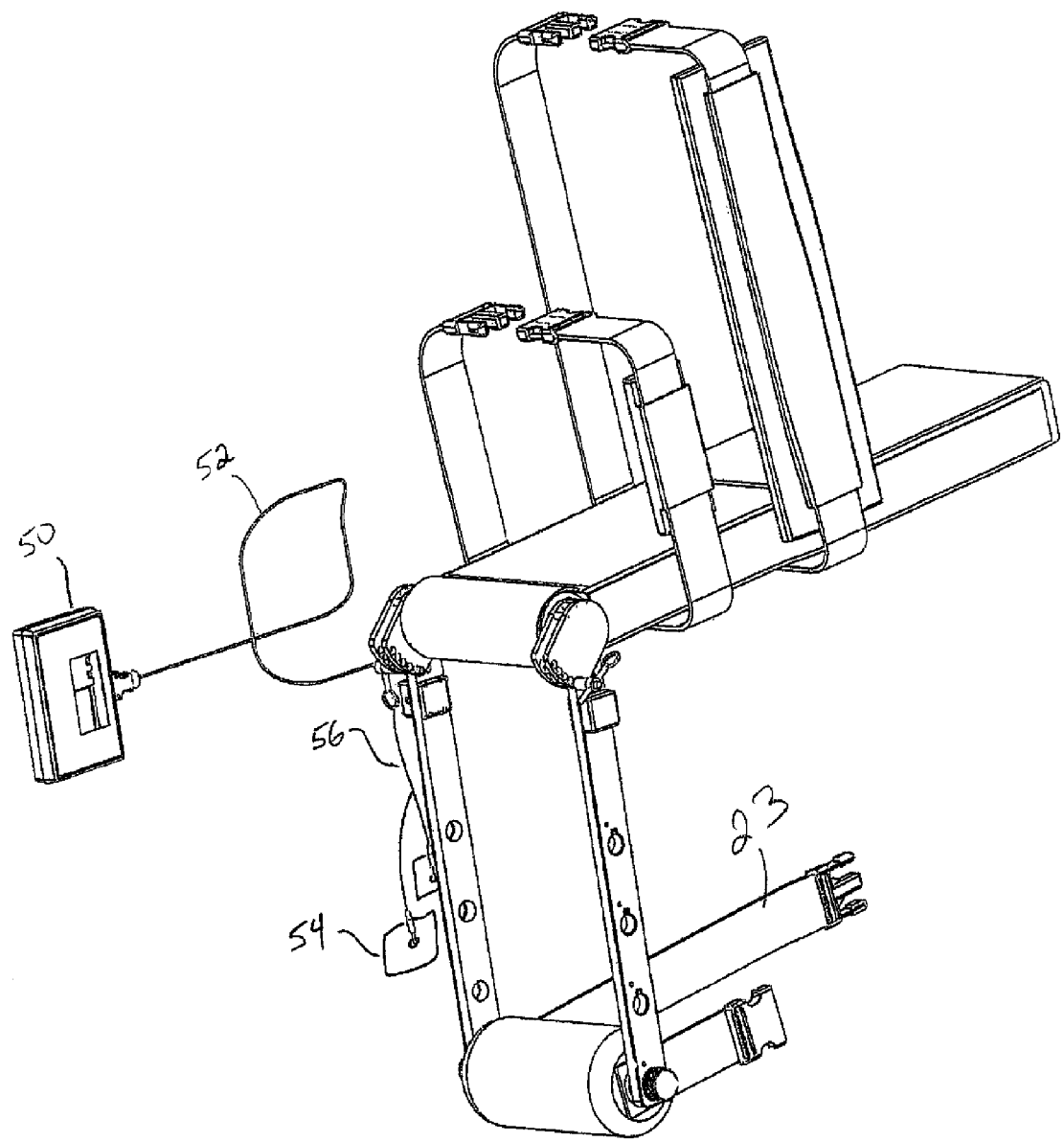
FIG. 2 is a perspective view of another embodiment thereof, including a controller.

The arms 20 may be adapted to allow the relative position of the cross member 22 to be adjusted. For example, one or more apertures 28 may be provided for receiving and positioning the cross member 22 at various positions along the extension 13 to compensate for subjects of various heights. A removable fastener 24 allows ease of adjustment of the position of the cross member 22 along the arms 20. As shown in FIG. 2, the extension 13 may further include a retainer, such as a strap 23, for further securing the subject's lower leg to the brace 10, such as along the calf, which again may help to ensure that an efficient isometric contraction is achieved.

The brace 10 may be adapted for fixing the seat 12 and extension 13 in position relative to one another. This may be achieved by providing a lock 18 for fixing the movement of the arms 20 relative to the hinge 16. In one aspect, and with reference to FIGS. 1*a* and 1*b*, the lock 18 may be in the form of a pin 26 for positioning in corresponding apertures 27 formed in pairs of spaced plates 29 associated with each arm 20 (and connected together by a cross member (not shown) extending through a passage formed in the rounded front end of the platform 15). The connection may be such that the lower portion and upper portions of the brace 10 are fixed against relative movement. In one such embodiment, pin 26 may pass through apertures 27 in spaced plates 29 as well as fixing aperture 27*a* in arm 20, thereby preventing relative movement between the upper and lower portions of the brace 10. This configuration is not limiting to the invention, as any other locking mechanism may be utilized which limits the degree of movement so as to ensure isometric contraction results.

In use, the brace 10 may be portable in nature and placed on a stable support surface, such as with the platform resting on the flat upper face of a chair or table. The subject may be positioned such that an upper leg rests on the support platform 15, with leg strap 14 attaching over the subject's upper leg, such as over the location of the quadriceps muscles. The subject's lower leg may extend through the extension 13, such that the subject's shin is placed behind the cross member 22. Optionally, a strap 23 may also be used to secure the lower leg in contact with the cross member 22, as shown in FIG. 2.

Figure 3:
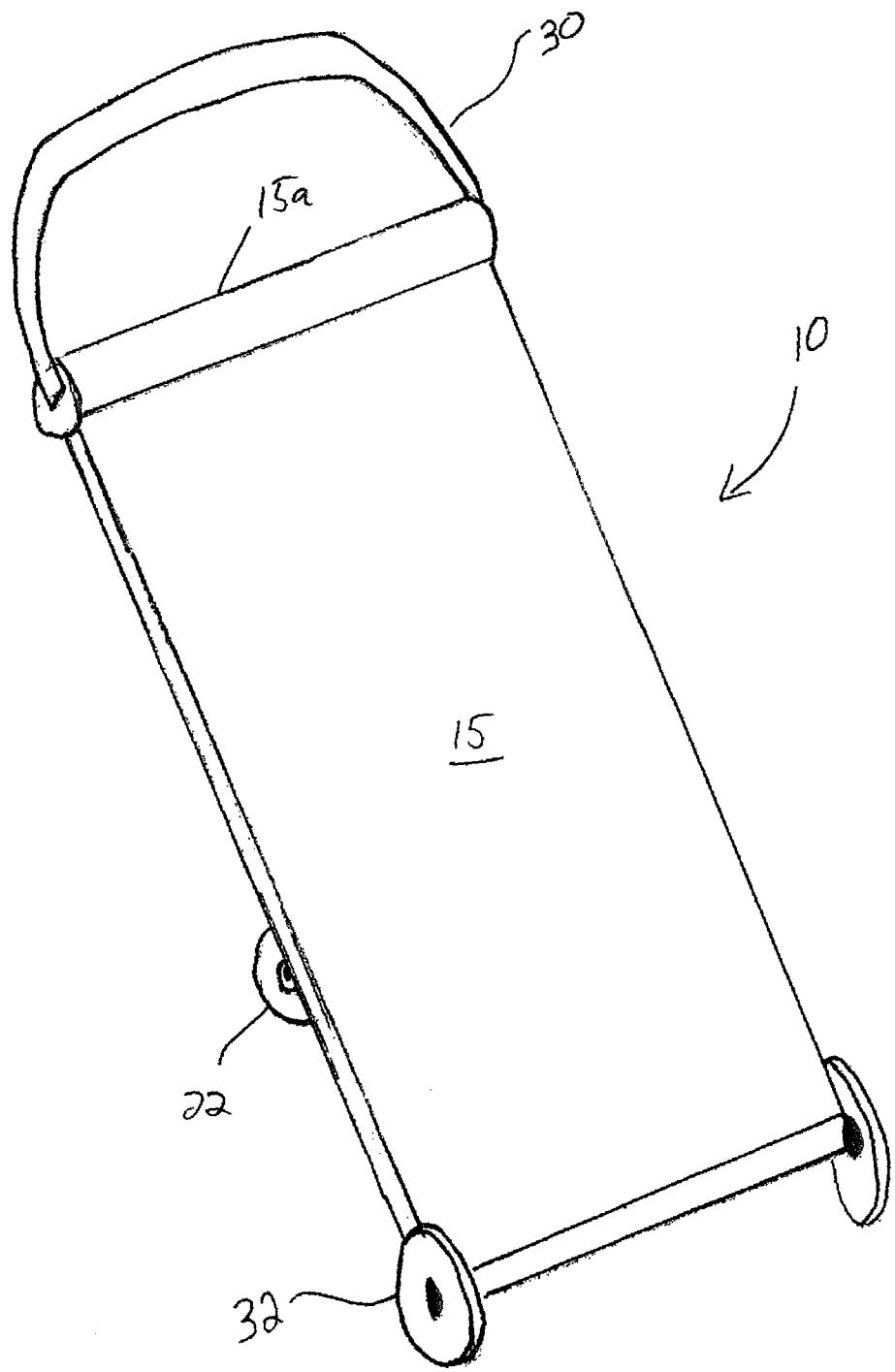
FIG. 3 is a perspective view of another embodiment thereof.

In one embodiment, illustrated in FIG. 3, the seat 12 and extension 13 are capable of rotating about 360 degrees relative to one another, and thus can be collapsed to a folded condition and locked in place. In this embodiment, the brace 10 may further include a handle 30 for ease of transport, which as illustrated may be provided adjacent the rounded end 15*a* of the platform 15. The brace 10 may additionally include wheels 32 at the opposite end for rolling transport, including in the folded condition. The relative positions of the handle 30 and wheels 32 may also be reversed from what is illustrated in FIG. 3, if desired.

In one particular embodiment, the brace 10 is instrumented. For example, the brace 10 may include at least one sensor 40 for sensing a force representative of the force exerted during the exercise movement (such as a torque associated with rotation or attempted rotation of the hinge 16 during the isometric exercise). The sensor 40 may be in the form of a strain gauge or any other sensor capable of measuring torque resulting from the attempted movement of the leg extension 13 relative to the seat 12 of the brace 10. The sensor 40 may be positioned along each arm 20 of the brace 10 and, as shown in FIGS. 1 and 2, may be provided at a location proximate the hinge 16 in a manner that avoids interfering with the leg position or the exercise in general.

As shown in FIG. 2, a pendant including a controller 50 may be associated with the brace 10. This controller 50 may be connected to the brace 10 via a connector, such as a control wire 52 or by way of a wireless connection, and may be powered by a power supply (not pictured). The controller 50 is configured to receive measurements from the sensor 40 with respect to the torque exerted by the subject during an exercise and control the stimulation applied to the subject at least partially based upon the measurements. The controller 50 may also be configured to store, analyze, and display the electrical stimulation provided to the subject as well as the measured force exerted on the brace 10, as measured by the sensor 40.

The brace 10 and controller 50 may be used in association with a stimulation circuit to stimulate the subject's muscles during an exercise such as in association with NMES. The stimulation circuit may be part of the pendant including the controller 50, part of the brace 10, or a separate external stimulator. Additionally, surface electrodes 54 may be used to transmit the stimulation signals to the subject's muscles. The electrodes 54 may be connected to the subject via connectors, such as electrode lead wires 56.

In any case, the controller 50 may be configured to monitor and manipulate the stimulation to the subject based at least partially on the force measured by the sensor 40. In one aspect, the controller may be configured to deliver predetermined pulse trains to the subject in order to cause contraction of the involved muscles. For example, the pulse trains may have amplitudes in the range of 0-200 mA and widths in the range of 0-1000 μs at frequencies in the range of 25-100 Hz. The controller 50 may further include adaptive stimulation control technology for autonomously developing outcome-based stimulation profiles customized to each subject and continually adjusted to produce repeatable biomechanical responses despite muscle fatigue, as outlined in the following description.

In practice, the NMES is generally provided in a series of cycles of electrical stimulation to the muscles, separated by periods of rest. A stimulation cycle includes a series of electrical pulses delivered to the patient's muscles. These cycles of stimulation and rest may last any amount of time. For example, the stimulation cycles may be provided for a relatively short period (e.g., approximately twelve seconds in one example), followed by a longer rest period (e.g., approximately sixty seconds), and then repeated. The number of stimulation cycles within a given exercise may vary.

These stimulation cycles may be provided in a "ramp-and-hold" pattern in which the stimulation intensity is quickly increased to a certain value which may be preset manually by a clinician, held at that value for the duration of the cycle, and then rapidly decreased to zero stimulation for a rest period. However, this ramp-and-hold method of stimulation may require significant input from a clinician and may provide only a marginal therapeutic benefit. Using an autonomous, adaptive stimulation control paradigm, such as by way of a controller 50 of the present invention, may decrease the number of cycles necessary to achieve the same result and/or provide greater therapeutic benefit to the patient, and may involve less attention by the clinician.

Accordingly, in one embodiment, a force goal is established, upon which therapeutic exercise stimulation values may be based. This force goal may be established prior to initiating therapeutic NMES. In one aspect, this force goal is based on a measurement of a maximum voluntary isometric contraction (MVIC) of the limb being stimulated. MVIC may be calculated by securing the affected leg in the brace 10 in a locked position, and measuring a torque associated with a maximum voluntary isometric contraction. The MVIC may be the mean steady torque computed over a portion of the contraction (e.g., the final five seconds). In the above embodiment, the force goal may range from about 20% to about 80% of MVIC. In the case of therapy following an ACLR, the force goal may nominally be 50% of MVIC, and in the case of a TKA, the nominal force goal may be 35% of MVIC. Alternatively, the force goal may be chosen by a medical provider or established by the subject at any particular desired value.

Figure 4:
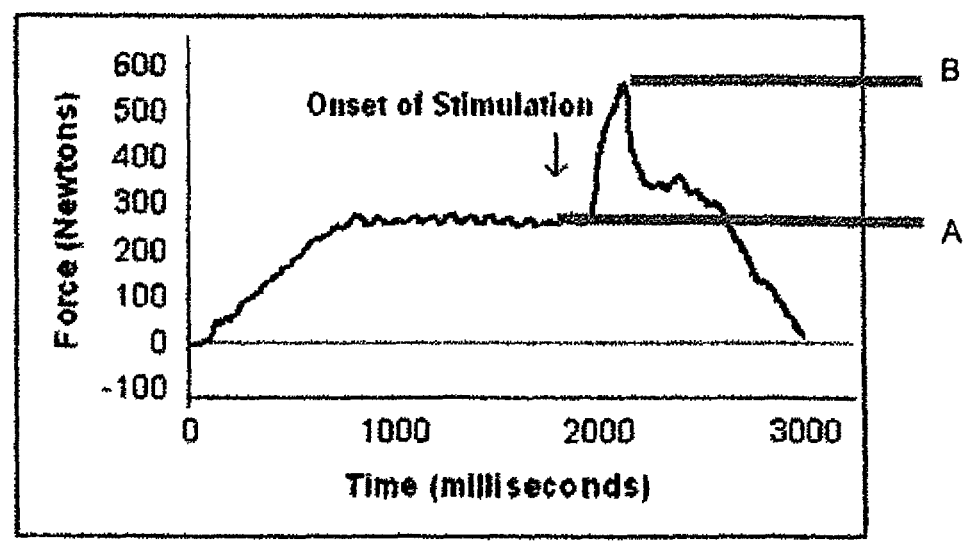
FIG. 4 is a graph of muscular stimulation according to on possible use of the disclosed device.

In one aspect of the invention, a central activation ration (CAR) may be calculated by comparing a muscle's MVIC to the muscle's maximum force generating capability, where the difference may be called the "volitional deficit." The change in CAR may be used to evaluate the strengthening of a muscle over time. The CAR may calculated through a burst superimposition protocol which is illustrated in FIG. 4. In this burst superimposition protocol, a patient is instructed to generate a maximum volitional contraction, at the end of which, a short burst of maximal stimulation may be delivered to the muscle. The patient's unstimulated MVIC is illustrated in FIG. 4 at "A," while the maximum force generated by the muscle under the burst of maximal stimulation is illustrated at "B." As the ratio of A to B (i.e. CAR) rises and approaches a value of 1, this indicates that the patient is better able to control the muscle. Routine exercise using the invention may improve CAR.

Figure 5:
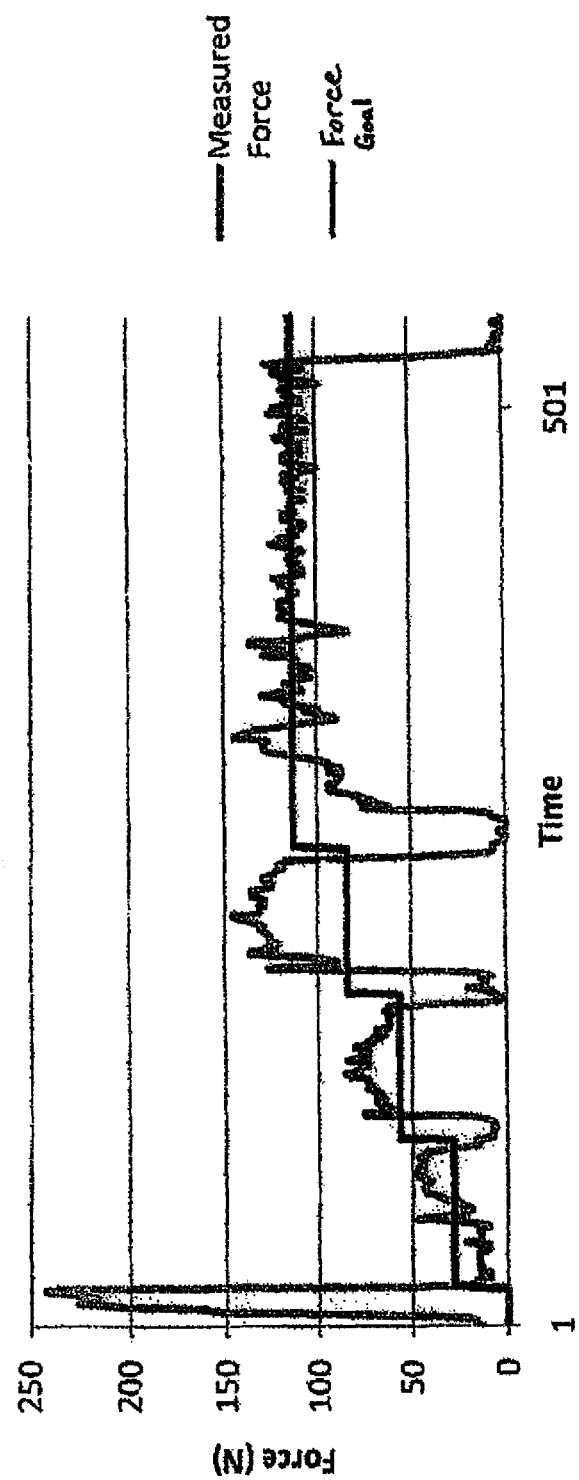
FIG. 5 is a graph of muscular stimulation according to another possible use of the disclosed device.

In a particular embodiment, the exercise may begin with a series of warm-up cycles. Initially, the limb, such as leg, upon which NMES is applied may be secured in the brace 10 in a fixed position. While any position may be chosen, it may be that the brace 10 is locked such that the joint is in about 60 degrees to about 65 degrees flexion. As illustrated in FIG. 5, the MVIC is initially measured at 226N, and a force goal during the therapeutic range is chosen to be 50% of MVIC (113N).

The series of warm-up cycles may comprise having the controller 50 provide an initial electrical stimulation to the subject's limb to elicit a contraction that causes a measurable force in the sensor 40. This initial warm-up cycle may be only a fraction of the therapeutic force goal. One or more further warm-up cycles may be provided with progressively stronger electrical stimulation in order to elicit progressively stronger contractions, until the measured force caused by the muscle contraction at sensor 40 reaches the goal force. Alternatively, stimulation may be automatically and quickly increased during each cycle until the desired force level is achieved. Stimulation may then be held at this level until the warm-up cycle ends. Each successive warm-up contraction may be used as the starting point for the next warm-up cycle. The number of warm-up cycles may vary, but only a small number of warm-up cycles and cycles having short duration may be used to avoid a significant number of exercise cycles outside of a therapeutic range. For example, only three warm-up cycles lasting three seconds may be needed to elicit a measured force that approximates the force goal.

The exercise regimen may include any number of exercise cycles in a therapeutic range, wherein the controller 50 may adjust the stimulation based at least partially on fatigue of the subject's muscles during the exercises. As the muscles fatigue, the same stimulation levels normally result in a lower measured force output over subsequent cycles. The disclosed implementation compensates for this lowered measured force output by comparing the force measured by sensor 40 with the force goal, and increasing the stimulation provided to the subject as needed in order to make the measured force approximate the force goal. During the therapeutic cycles, the controller 50 may utilize any number of processes in order to make the measured force approximate the goal force. As few as ten therapeutic cycles may be needed in a given exercise period to achieve muscle strengthening.

A first process for controlling muscular output may involve calculating an average measured force in one cycle and comparing that average measured force to the force goal. If the average measured force is less than the force goal, then the stimulation in the subsequent cycle is increased in order to increase the contraction intensity in the subsequent cycle. Alternately, if the average measured force is greater than the force goal, then the stimulation in the subsequent cycle is decreased in order to decrease the contraction intensity in the subsequent cycle. The amount of decrease may be proportionally smaller than the amount of increase due to anticipated muscle fatigue. In one aspect, a decrease in stimulation in response to a measured force greater than the goal force may be one eighth of a corresponding increase in stimulation in response to a measured force less than the goal force. The measured and goal forces may be in the form of torque on the brace caused by contraction of the leg muscles.

The increase or decrease in stimulation may be tempered by a learning rate designed to cause the measured torque to approximate the goal torque in a more accurate manner. This process may be referred to as a "feed forward" control. The feed forward control may be mathematically represented below:

$$FF_{n+1} = FF_n + \frac{\text{Goal} - AverageTorque_n}{\text{Goal}} * LearningRate$$

where $FF_{n+1}$ is the stimulation level supplied by the feed forward control in the $(n+1)^{th}$ cycle; $FF_n$ is the stimulation level supplied by the feed forward control in the $n^{th}$ cycle; "Goal" is the torque goal; "$AverageTorque_n$" is the average torque measured during the $n^{th}$ cycle; and "LearningRate" is the rate at which the feed forward control may increase or decrease the stimulation from one cycle to the next.

The feed forward control is illustrated in FIGS. 6a and 6b. During a first cycle, a first level of stimulation is provided to the subject's leg, as shown in FIG. 6a. This elicits a contraction in the leg which causes a torque that is measured in sensor 40, as shown in the decreasing torque value in the first cycle of FIG. 6b. The controller 50 calculates an average measured torque during the first cycle, and compares it to a torque goal. In this embodiment, the torque goal has been set at 60% MVIC. Because the average measured torque in the first cycle is less than the torque goal, the second level of stimulation in the second cycle of FIG. 6a is greater than in the first cycle.

This results in a greater average measured torque in the second cycle as shown in FIG. 6b, which more closely approximates the torque goal.

In a second process for controlling muscular output, referred to as a feedback control, the controller 50 may adjust the stimulation intensity within a cycle based at least partially on a measured force within that cycle. The measured force at a given time during a cycle may then be compared to the force goal. If the measured torque exceeds the goal, then the stimulation within that cycle may be decreased in response. This may be necessary in order to avoid over stimulating a muscle which may cause early fatigue, or as a safety mechanism to protect the joint.

Alternately, if the measured force at a given time during a given cycle is less than the goal, such as due to fatigue, then stimulation within that cycle may be increased in order to compensate for the fatigue. The stimulation may be adjusted at a specified number of intervals within a cycle, or may be continually adjusted based on real-time measurements of force within the cycle. In one embodiment, both the feedback control for decreasing stimulation and the feedback control for increasing stimulation may be utilized simultaneously. Both controls may also be excluded from acting if a measured force sufficiently approximates a force goal, such as if the measured force is within +1-20% of the force goal.

In one aspect, as a muscle experiences fatigue during a cycle, the contraction intensity decreases over time and the measured force also decreases over time. The controller 50 may evaluate how the measured force compares to the goal at one time interval and adjust the stimulation intensity based thereon in an effort to cause the measured force to approximate the force goal. One embodiment of the feedback control may be represented mathematically below:

$$FB_{i+1} = FB_i + \sum_{i=FirstPointAboveThresholdForce}^{EndOfCycle-1sec} \left(\frac{Goal - Torque_i}{Goal}\right) * K$$

where $FB_{i+1}$ is the stimulation level provided by the feedback control during the $(i+1)^{th}$ time interval within a given cycle; $FB_i$ is the stimulation level provided by the feedback control during the $i^{th}$ time interval within the cycle; Goal is the goal torque; $Torque_i$ is the measured torque at the $i^{th}$ time interval within the cycle; and K is a constant to regulate the rate at which the feedback control may increase or decrease the stimulation level from one time interval to the next. In this embodiment, the measured torque is compared to the goal torque at each time point from the first point the measured force crosses the threshold value until one second before the end of the cycle, the point at which stimulation begins to "ramp down." Each subsequent time interval within a cycle may be adjusted based on the measured torque at the immediately preceding time interval within that cycle.

This feedback control is illustrated in FIGS. 7a and 7b. In this embodiment, an initial warm-up cycle gradually increases the stimulation until a value of the measured torque equals the torque goal, which is illustrated as 60% MVIC. The stimulation may be maintained at that initial level for the duration of the warm-up cycle. In the first therapeutic cycle, which immediately follows the initial warm-up cycle, the stimulation is set at the initial level determined during warm-up. Due to fatigue within that cycle, this measured torque decreases at a certain rate over the course of the first therapeutic cycle.

In contrast, during the second therapeutic cycle (the last cycle illustrated in FIGS. 7a and 7b), the controller 50 utilizes the feedback control to adjust the stimulation to the muscles. This feedback control compares the measured torque at each point of time over the course of the second therapeutic cycle to the torque goal and adjusts the stimulation at each subsequent point of time within the second therapeutic cycle in order to cause the measured torque to more closely approximate the torque goal. Here, the intensity of the stimulation within the second therapeutic cycle may gradually increase throughout the course of the cycle at a certain rate to compensate for the muscle fatigue such as that which was present in the first therapeutic cycle.

In one embodiment, the feedback control may only engage if a measured torque deviates from the torque goal by a predetermined or threshold amount. For example, this threshold amount may be a relatively small percentage (e.g., 20%) of the torque goal. In this embodiment, in the event that the measured torque deviates from the torque goal by less than the threshold amount, the stimulation will remain at the same stimulation level until the deviation reaches the threshold amount.

The controller 50 may utilize either the feed forward or feedback control processes for controlling muscular output alone, or in combination with one another to create an autonomous, adjustable NMES system to account for overstimulation and/or muscular fatigue. In the embodiment in which the feed forward and feedback controls are used in combination, the stimulation intensity at any given time interval within a cycle may be a function of the stimulation provided through the feed forward control (which is itself a function of the average measured force of the previous cycle) and the stimulation provided through the feedback control (which is itself a function of the measured force at the immediately previous time interval within that cycle). This can be represented mathematically as follows:

$$Z_i = FF_n + FB_i$$

where $Z_i$ is the stimulation intensity at the $i^{th}$ interval within the $n^{th}$ cycle; $FF_n$ is the stimulation provided through the feed forward control for the $n^{th}$ cycle and is a function of the measured torque in the $(n-1)^{th}$ cycle; and $FB_i$ is the stimulation provided through the feedback control at the $i^{th}$ interval within the $n^{th}$ cycle.

In one embodiment wherein the feed forward and feedback controls are used in combination, the measured torque which is used to determine the stimulation contributed through the feed forward control may be based on the portion of the previous cycle prior to engagement of the feedback control. More specifically, the average measured torque in the $n^{th}$ cycle which is used to calculate a feed forward stimulation intensity for the $(n+1)^{th}$ cycle may only account for the measured torque in the portion of the $n^{th}$ cycle in which the feedback control did not contribute any stimulation. Alternatively, the feed forward control in the $(n+1)^{th}$ cycle may only account for a minimum or maximum measured torque in the portion of the $n^{th}$ cycle in which the feedback control did not contribute any stimulation, rather than accounting for an average measured torque. In another embodiment, one or both of the feedback controls, or the feed forward control may be manually disabled by the patient or a clinician.

Figure 8:
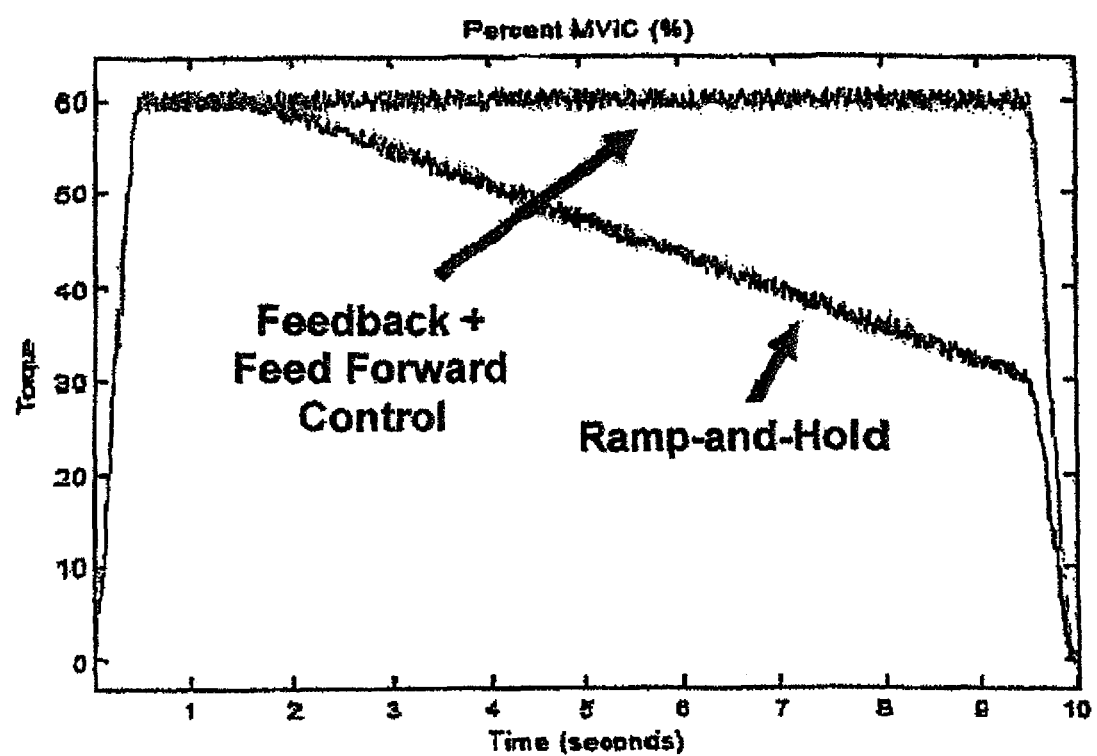
FIG. 8 is a graph of measured force as compared to a "ramp-and-hold" method of stimulation.

The combination of feedback and feed forward controls offers certain advantages over the traditional "ramp and hold" approach to neuromuscular stimulation, one of which is a more efficient therapeutic exercise. As can be seen in FIG. 8, the controller 50 adapted to use the above-described technique allows for a muscular output with an accurate approximation of a goal force. The adjusted stimulation generated can lead to as much as a 30% increase in a cycle torque (see FIG. 8) as compared to a ramp-and-hold stimulation waveform.

The foregoing descriptions of various embodiments of the invention are provided for purposes of illustration and not intended to be exhaustive or limiting. Modifications or variations are also possible in light of the above teachings. For instance, the controller 50 could be utilized with a brace for isolating another portion of the subject's body for isometric muscle contractions, such as the arm in a therapeutic method for elbow rehabilitation or perhaps a wrist. Additionally, the muscular control processes utilized by the controller 50 may be used in association with dynamic contractions. The embodiments described were chosen to provide the best application to thereby enable one of ordinary skill in the art to utilize the disclosed inventions in various embodiments and with various modifications as are suited to the particular use contemplated. All such modifications and variations are within the scope of the disclosure.

The invention claimed is:

1. A device for use by a human subject in a seated, upright condition in conjunction with one or more electrodes for transmitting electrical stimulation to at least one muscle of a leg to perform an isometric contraction of the muscle, said device comprising:
    a brace including a seat adapted for receiving and supporting an upper portion of the leg of the subject in the seated, upright condition, the brace including a lower extension depending from the seat and configured to constrain a lower portion of the leg in order to allow the isometric contraction of the muscle to be achieved;
    a stimulator for transmitting electrical stimulation to at least one muscle to cause the isometric contraction of the muscle; and
    a controller for controlling the stimulation through the electrodes based at least partially on the sensed force;
    wherein the controller is adapted to use an adaptive feed forward control algorithm to compare a sensed force during a first contraction cycle to a predetermined force goal and to adjust the stimulation during a subsequent contraction cycle based on said sensed force.

2. The device of claim 1, further including a hinge adapted for fixing the lower extension relative to the seat and determining an amount of knee flexion during the isometric contraction.

3. The device of claim 1, wherein the lower extension includes at least one arm supporting a transverse member for engaging a front side of the lower leg, the position of the transverse member being adjustable along the lower extension.

4. The device of claim 3, wherein the seat comprises a first end portion adapted for positioning adjacent a rear surface of the subject's knee joint while the transverse member engages the front side of the lower leg.

5. The device of claim 1, further including at least one strap for securing the upper portion of the leg to the seat.

6. The device of claim 1, further including a sensor for sensing a force exerted against the brace during or resulting from the isometric contraction.

7. The device of claim 1, wherein the controller is further adapted to use a feedback control algorithm to compare the sensed force within the contraction cycle to a predetermined force goal, and if the sensed force is below the predetermined force goal, increase the stimulation within that contraction cycle based on the sensed force.

8. A method for stimulating a leg of a human subject to cause an isometric contraction in at least one leg muscle, comprising:
    constraining the movement of the subject's leg using a brace, the subject being seated at least partially along an upper portion of the brace connected to a lower portion of the brace for receiving the subject's lower leg;
    electrically stimulating the subject's leg with a first pulse train during a first cycle in order to cause the isometric contraction and urge the lower leg against the lower portion of the brace;
    measuring a torque exerted by the leg during the first cycle; and
    adjusting a second pulse train during a second cycle to stimulate the subject's leg at a stimulation level based at least partially on the measured torque during the first cycle.

9. The method of claim 8, wherein the adjusting step comprises comparing an average measured torque during the first cycle to a goal torque.

10. The method of claim 8, further including measuring a torque during the second cycle, and wherein the adjusting step further includes adjusting the second pulse train based at least partially on the measured torque during the second cycle.

11. The method of claim 10, wherein the adjusting step comprises comparing the measured torque during the second cycle to a goal torque and increasing or decreasing the stimulation level of the second pulse train to cause the measured torque to approximate the goal torque.

12. The method of claim 11, wherein the comparing step comprises comparing the measured torque to the goal torque at a series of time intervals within the second cycle.

13. The method of claim 8, further including the step of providing an initial warm-up cycle that gradually increases the stimulation until a value of the measured torque equals a goal torque, wherein a stimulation during the first pulse train is at least partially based on the stimulation during the warm-up cycle.

14. The method of claim 8, further including the step of increasing the stimulation during the second cycle to compensate for fatigue.

15. The method of claim 8, further including the step of fixing the leg at between about 60 degrees to about 65 degrees of knee flexion.

16. A method for adaptively stimulating a limb of a human subject during a series of neuromuscular electrical stimulation cycles, each cycle comprising a train of stimulation pulses, said method comprising providing a brace adapted for:
    electrically stimulating the limb in a first cycle using a first pulse train to elicit a muscular contraction;
    determining an actual force applied by the muscular contraction during the first cycle; and
    electrically stimulating the limb at a first time interval in a second cycle using a second pulse train different from the first pulse train to stimulate the limb based at least partially on the actual force determined during the first cycle.

17. The method of claim 16, further including the step of increasing the stimulation at a second time interval in the second cycle in response to the measured force at the first time interval being lower than a goal force, and decreasing the stimulation at the second time interval in response to measured force at the first time interval being greater than the goal force.

18. The method of claim 16, wherein the step of determining an actual force includes the step of calculating an average measured force in the first cycle, and the second stimulation step comprises comparing that average measured force to the goal force.

19. An instrumented brace for adaptively stimulating a limb of a human subject during a series of neuromuscular electrical stimulation cycles, each cycle comprising a plurality of stimulation pulses, said brace comprising:
- a sensor for measuring a force exerted by the subject on the brace; and
- a controller adapted for electrically stimulating the limb in a first cycle using a first pulse train to elicit a muscular contraction, and for electrically stimulating the limb at a first time interval in a second cycle using a second pulse train different from the first pulse train to stimulate the limb based at least partially on a measured force during the first cycle.

20. The brace of claim 19, wherein the controller is further adapted to increase the stimulation at a second time interval in the second cycle in response to the measured force at the first time interval being lower than a goal force, and decreasing the stimulation at the second time interval in response to measured force at the first time interval being greater than the goal force.

21. The brace of claim 19, wherein the controller is further adapted to calculate an average measured force in the first cycle, and to provide the stimulation at the first time interval in the second cycle based on a comparison of the average measured force during the first cycle to the goal force.

22. The brace of claim 20, wherein the controller is further adapted to only increase or decrease the stimulation at the second time interval in the second cycle based on the measured force at the first time interval of the second cycle when the measured force at the first time interval in the second cycle differs from the goal force by greater than a threshold amount.

* * * * *